US009675282B2

(12) United States Patent
Morren

(10) Patent No.: US 9,675,282 B2
(45) Date of Patent: Jun. 13, 2017

(54) METHOD AND APPARATUS FOR DETERMINING A RESPIRATION SIGNAL

(75) Inventor: Geert Guy Georges Morren, Vissenaken (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1137 days.

(21) Appl. No.: 13/575,969

(22) PCT Filed: Feb. 7, 2011

(86) PCT No.: PCT/IB2011/050512
§ 371 (c)(1),
(2), (4) Date: Jul. 30, 2012

(87) PCT Pub. No.: WO2011/098944
PCT Pub. Date: Aug. 18, 2011

(65) Prior Publication Data
US 2012/0296221 A1    Nov. 22, 2012

(30) Foreign Application Priority Data

Feb. 11, 2010   (EP) .................................... 10153269

(51) Int. Cl.
*A61B 5/113*        (2006.01)
*A61B 5/00*         (2006.01)

(52) U.S. Cl.
CPC .............. *A61B 5/113* (2013.01); *A61B 5/721* (2013.01); *A61B 2562/0219* (2013.01)

(58) Field of Classification Search
None
See application file for complete search history.

(56) References Cited

U.S. PATENT DOCUMENTS 5,974,340 A * 10/1999 Kadhiresan ........ A61N 1/36542
                                                                607/18
6,064,910 A *  5/2000 Andersson et al. ............ 607/20
(Continued)

FOREIGN PATENT DOCUMENTS

JP    2006068091 A    3/2006
JP    2006247374 A    9/2006
(Continued)

OTHER PUBLICATIONS

Jin, A., et al.; Performance Evaluation of a Tri-axial Accelerometry-based Respiration Monitoring for Ambient Assisted Living; 2009; 31st Annual International Conference of the IEEE EMBS, Minneapolis, MN, USA; pp. 5677-5680.
(Continued)

*Primary Examiner* — Jacqueline Cheng
*Assistant Examiner* — Jairo Portillo

(57) ABSTRACT

The invention relates to a method and apparatus for determining a respiration of a subject (305) in which, with a single multi-axial accelerometer (310) positioned on a body of the subject (305), accelerometer signals are generated (101) indicative of the acceleration of the subject (305) along different spatial axes, a vector magnitude signal of the acceleration of the subject (305) along the different spatial axes is calculated (102) from the accelerometer signals, a non-respiratory motion contribution to the acceleration along the different spatial axes is identified (103, 203) from the vector magnitude signal, which non-respiratory motion contribution is not caused by the respiration, and a respiration signal indicative of the respiration of the subject is determined (104, 204) by filtering the non-respiratory motion contribution from at least one of the accelerometer signals. In this way a method is provided which determines
(Continued)

the respiration of a subject (305) with a single accelerometer (310) in an efficient and, for a patient, comfortable way.

20 Claims, 7 Drawing Sheets

(56) References Cited

U.S. PATENT DOCUMENTS

| | | | |
|---|---|---|---|
| 6,997,882 B1* | 2/2006 | Parker et al. | 600/534 |
| 7,041,062 B2* | 5/2006 | Friedrichs et al. | 600/534 |
| 7,267,652 B2* | 9/2007 | Coyle et al. | 600/538 |
| 7,634,379 B2* | 12/2009 | Noble | 702/141 |
| 7,727,161 B2* | 6/2010 | Coyle et al. | 600/538 |
| 7,766,841 B2 | 8/2010 | Yamamoto et al. | |
| 2003/0018248 A1* | 1/2003 | Kreger | A61B 5/0456 600/413 |
| 2004/0204638 A1* | 10/2004 | Diab et al. | 600/336 |
| 2005/0119586 A1* | 6/2005 | Coyle et al. | 600/538 |
| 2007/0118054 A1* | 5/2007 | Pinhas et al. | 600/587 |
| 2008/0214963 A1 | 9/2008 | Guillemaud et al. | |
| 2010/0010380 A1* | 1/2010 | Panken et al. | 600/587 |
| 2010/0030085 A1* | 2/2010 | Rojas Ojeda | A61B 5/0205 600/484 |

FOREIGN PATENT DOCUMENTS

| | | |
|---|---|---|
| WO | 03005893 A2 | 1/2003 |
| WO | 2010145009 A1 | 12/2010 |

OTHER PUBLICATIONS

Thakor, N. V., et al.; Applications of Adaptive Filtering to ECG Analysis: Noise Cancellation and Arrhythmia Detection; 1991; IEEE Trans. on Biomedical Engineering; 38(8)785-794.
Tong, D. A., et al.; Adaptive Reduction of Motion Artifact in the Electrocardiogram; 2002; Proceedings of the 2nd joint EMBS/BMES Conference; vol. 2:1403-1404.
Yang, Y-S O., et al.; Adaptive Reduction of Motion Artefact in Wireless Physiological Monitoring Microsystems; 2008; 3rd International Conference on Sensing Technology; pp. 523-526.
Kaist; Motion artifact reduction with active noise cancellation and acceleerometer for wearable Photoplethysmography; Korea Advanced Institute of Science & Technology; downloaded Jan. 22, 2010; http://medev.kaist.ac.kr/upload/paper/MT02.pdf.

* cited by examiner

Time [seconds]

METHOD AND APPARATUS FOR DETERMINING A RESPIRATION SIGNAL

FIELD OF THE INVENTION

The invention relates to a method and apparatus for determining a respiration signal.

BACKGROUND OF THE INVENTION

Respiration rate has proven to be a good indicator of the deterioration of the condition of a patient and it plays a crucial role in early warning hospital systems in combination with other vital body signs. Therefore, a need for continuous and reliable monitoring of a respiration signal is seen especially in the intensive care units of hospitals. A similar need, with less stringent requirements on the instantaneous presentation of the monitored parameters, is present in the general ward settings of hospitals and in home healthcare applications, such as in telemedicine and chronic disease management. While continuous monitoring of the respiration signal, from which the respiration rate is extracted, is available on bedside monitors for intensive care patients, various portable sensor systems are being developed to allow unobtrusive and prolonged measurement and monitoring of the respiration signal of mobile patients in general wards with minimal discomfort.

Respiratory monitoring can be based on different principles: the measurement of respiratory effort, for example thorax impedance plethysmography, accelerometers, photoplethysmography, or the measurement of respiratory effect, for example sound recording, temperature sensing, carbon dioxide sensing. Some sensors are already well established to monitor respiration in applications other than general ward. In intensive care units for example, thorax impedance-plethysmography is the method of choice, whereas in sleep studies inductive plethysmography, often referred to as respiration band, is also commonly used. In ambulatory patients, such as on the general ward or in home healthcare, these sensors have limitations. A respiration band, for example, is considered to be too obtrusive by both medical personnel and patients.

A respiration monitoring system based on a multi-axial accelerometer overcomes this disadvantage. A multi-axial accelerometer is a device that measures the acceleration in multiple sensing axes, and is used as an inclinometer to reflect the abdomen or chest movement caused by respiration. This technique requires reliable signal processing methods to enable reliable monitoring under different conditions and postures of the patient.

Motion artifact is a well known issue in patient monitoring as a whole, which refers to the contamination of the physiological signal and the degradation of the measurement quality caused by physical activities of a patient, such as posture change, movement and talking. The motion artifact issue is more pronounced in a general ward setting than in an intensive care unit setting, since patients in the general ward setting generally have a more mobile activity pattern and are monitored most of the time without supervision of hospital staff, thus lacking knowledge on the presence of physical activities. The problem becomes even more severe in the monitoring of patients in home healthcare settings.

If a multi-axial accelerometer is used to measure respiration rate in ambulatory conditions such as home healthcare or patients on a general ward, the accelerometer signals do not only change due to the respiration of a person but the accelerometer signals are also affected by unwanted motions, that are not caused by respiratory motions, such as whole-body movements, such as for example walking or running, and other physiological motions, such as for example due to heart beat. Some of these unwanted motions, which may have frequency components in the same range of the respiration, i.e. 0.1 Hz to 2 Hz or 6 respirations per minute to 120 respirations per minute, cannot be suppressed with a filter with a fixed frequency response.

U.S. Pat. No. 6,997,882 B1 discloses a method and device for processing accelerometer data to derive information about the respiratory movements of a subject. The method applies an array of four uni-axial accelerometer modules worn on the pelvis of a subject and separates the acceleration of the anterior aspect of the pelvis from the posterior aspect of the pelvis. The fundamental premise of this approach is that respirations have a disproportionate effect on the anterior aspect of pelvic motion, which can be exploited using a differential technique. In particular, the isolation of a high signal-to-noise ratio respiratory signal is accomplished using an adaptive noise-cancellation algorithm that employs the least means square filtering technique. The approach treats the net acceleration in the summed (horizontal plane) anterior accelerometer channels as representing the signal of interest, i.e. acceleration due to respirations, plus noise, whereas the summed (horizontal plane) posterior accelerometer signal represents mainly noise, which is, however, highly correlated with the noise in the composite anterior accelerometer signal. The noise is due mainly to accelerations caused by motion of the pelvis in the transverse plane, such as during sway, walking, and running. A disadvantage of this method is that it requires an array of accelerometer modules which have to be worn by a subject.

SUMMARY OF THE INVENTION

It is an object of the present invention to provide a method and an apparatus which determines the respiration signal with an accelerometer in an efficient and, for a patient, comfortable way.

In a first aspect of the present invention a method for determining respiration of a subject comprises the steps of:
generating, with a single multi-axial accelerometer positioned on a body of the subject, accelerometer signals indicative of the acceleration of the subject along different spatial axes,
calculating a vector magnitude signal of the acceleration of the subject along the different spatial axes from the accelerometer signals,
identifying from the vector magnitude signal a non-respiratory motion contribution to the acceleration along the different spatial axes which non-respiratory motion contribution is not caused by the respiration,
determining a respiration signal indicative of the respiration of the subject by filtering the non-respiratory motion contribution from at least one of the accelerometer signals.

With the method according to the invention, the respiration of a subject, for example a human person, is determined with only one multi-axis accelerometer positioned on the body of the subject. Thus the signals and data that are acquired only by the single multi-axial accelerometer are sufficient to determine the respiration of the subject. No external signals or other reference sensors, such as a reference heart beat sensor or a second multi-axial accelerometer, are required to determine the respiration. The respiration is determined in a comfortable way for the subject or patient, because it involves only one multi-axial accelerometer positioned on the body of the patient which acquires acceleration signals that are indicative of the acceleration of the subject. For a static, i.e. not-moving, multi-axial accelerometer the vector magnitude is always the same irrespective of the orientation of the sensor. This shows that the orientation of the sensor on itself does not affect the vector magnitude. If the orientation of the accelerometer changes due to whole body movements, for example walking, however, this is almost always accompanied by an inertial component in or contribution to the acceleration. For slow, smooth movements, such as respiration, this inertial component is small with respect to the orientation change. On the other hand for impulse-like vibrations, such as cardiac pulsation, the inertial contribution to the acceleration is larger than the orientational contribution of the acceleration. The accelerometer signal changes associated with respiration are mainly due to orientation changes with relation to the gravity direction and to a much smaller extent due to inertial acceleration, because the respiration movement of, for example, the thorax, is a slow, smooth movement. Many types of movement, such as walking or the heart beat of the subject, have a larger inertial contribution to the accelerometer signals than the inertial contribution due to respiration. For example, the heart beat can be identified by short bursts of rapid fluctuations of the thorax. The vector magnitude of the accelerometer signals provides for an efficient way of identifying the unwanted or non-respiratory motion contributions to the acceleration signals, because the vector magnitude of the accelerometer signals is a representation of the inertial acceleration components. The identified non-respiratory motion contribution, which motion is not due to the motion of the body of the subject caused by respiration, is then used to suppress and filter this unwanted motion contribution from at least one of the accelerometer signals. From the at least one filtered accelerometer signal, a respiration signal is determined that reliably and accurately represents the respiration of the subject and wherein the non-respiratory, and unwanted, motion contribution to the acceleration signals, i.e. motion contribution that is not caused by a respiration motion, is filtered from the accelerometer signal.

In an embodiment of the method according to the invention, the step of determining the respiration signal includes the steps of filtering the non-respiratory motion contribution from each of the accelerometer signals separately, and determining the respiration signal from a combination of the filtered accelerometer signals. According to this embodiment all accelerometer signals are filtered and then combined into a single filtered accelerometer signal from which the respiration signal is determined. This provides for a more accurate representation of the respiration irrespective of the orientation of the body of the subject, because the accelerometer signals from all different spatial axes are used in all the method steps to determine the respiration signal.

In an embodiment of the method according to the invention, the step of identifying the non-respiratory motion contribution comprises a step of extracting a characteristic frequency of the non-respiratory motion contribution from the vector magnitude signal. The characteristic frequency provides a straightforward parameter that can be used to filter the non-respiratory motion contribution from the accelerometer signals. The characteristic frequency is a frequency that is characteristic for the non-respiratory motion, for example it is the fundamental frequency of the non-respiratory motion. Higher harmonics of the fundamental frequency of the non-respiratory motion can also be extracted from the vector magnitude signal and subsequently used to filter the non-respiratory motion from the accelerometer signals.

In an embodiment of the method according to the invention, the step of identifying the motion contribution comprises a step of extracting a noise reference signal representative for the unwanted noise contribution from the vector magnitude signal. The noise reference signal is a signal that represents the non-respiratory motion signal component in or contribution to the accelerometer signals and can advantageously be used in the further processing of the accelerometer signals, for example to filter the non-respiratory motion contribution from the accelerometer signals.

In a further embodiment the noise reference signal is extracted from the vector magnitude signal with a digital filtering technique. This is a simple and efficient way of extracting the noise reference signal. For example, the envelope is calculated from the vector magnitude signal to extract the noise reference signal. In another further embodiment the noise reference signal comprises a cardiac interference signal. In this way the unwanted cardiac interference can be removed from the accelerometer signals. In another further embodiment the step of determining the respiration signal comprises a step of filtering the accelerometer signals with an adaptive noise filter with the noise reference signal. An adaptive noise filter provides for an efficient and reliable way of filtering the non-respiratory motion contribution from the accelerometer signals. In another further embodiment the step identifying the non-respiratory motion contribution further comprises a step of extracting a characteristic frequency of the non-respiratory motion contribution from the noise reference signal and wherein the step of determining the respiration signal comprises a step of filtering the characteristic frequency from the accelerometer signals with an adaptive notch filter. This provides for a straightforward filtering non-respiratory motion using the characteristic frequency from the accelerometer signals. Alternatively, a comb filter can be applied in the step of filtering the characteristic frequency in which case also higher harmonics are filtered.

In an embodiment of the method according to the invention, the step of identifying the non-respiratory motion contribution comprises the steps of:

calculating a power spectrum of the vector magnitude signal, extracting a characteristic frequency of the non-respiratory motion from the power spectrum, and wherein the step of determining the respiration signal comprises a step of filtering the characteristic frequency from the accelerometer signals with an adaptive notch filter.

The power spectrum represents the magnitude of the Fourier transformed vector magnitude signal. Thus this embodiment provides a simple and reliable way to identify the relatively large inertial components in the accelerometer signals that are due to a non-respiratory motion of the body of the subject.

In an embodiment of the method according to the invention, the step of identifying the motion contribution comprises the steps of:

calculating a coherence spectrum of the vector magnitude signal and one of the accelerometer signals, extracting a characteristic frequency of the non-respiratory motion contribution from the coherence spectrum, and wherein the step of determining the respiration signal comprises a step of filtering the characteristic frequency from the accelerometer signals with an adaptive notch filter.

The coherence spectrum indicates how well the vector magnitude signal corresponds to or matches with one of the accelerometer signals at each frequency. The frequency component with the highest coherence is considered to be the non-respiratory motion signal, because the inertial contribution in the accelerometer signals due to the non-respiratory motion is larger compared to the inertial contribution in the accelerometer signals due to the respiration motion.

In a further embodiment the characteristic frequency of the non-respiratory motion contribution comprises a heart beat frequency of the subject. Advantageously, in this way the frequency of the heart beat, i.e. the pulse rate, of the subject is determined simultaneously with the respiration of the subject from the accelerometer signals of one accelerometer positioned on the body of the subject.

In a further embodiment the characteristic frequency of the non-respiratory motion contribution comprises a step frequency of a moving subject. In this way the step frequency of a moving, i.e. walking or running, subject can be determined simultaneously with the respiration of the subject from the accelerometer signals of one accelerometer positioned on the body of the subject. In an embodiment the heart beat of the subject can be determined in addition to and simultaneously with the respiration and the step frequency.

In an embodiment of the method according to the invention, the method further comprises a step of extracting a respiration rate of the subject from the respiration signal. Because the respiration signal is available with a reduced non-respiratory motion contribution, the extracted respiration rate gives a reliable representation of the actual respiration rate.

In an embodiment of the method according to the invention, the method further comprises a step of filtering a frequency range from the vector magnitude signal which filtered vector magnitude signal is used in the step of identifying the non-respiratory motion contribution. By pre-filtering the vector magnitude signal, a more reliable and accurate method of determining the respiration signal is achieved. Preferably the frequency range covers the frequency range of the respiration of the subject.

In a second aspect of the present invention a respiration determination apparatus for determining respiration of a subject comprises:

a single multi-axial accelerometer for being positioned on a body of the subject, wherein the multi-axial accelerometer is adapted to generate accelerometer signals indicative of the acceleration of the subject along different spatial axes, a signal processing unit adapted for calculating a vector magnitude signal of the acceleration of the subject along the different spatial axes from the accelerometer signals and for identifying a non-respiratory motion contribution to the acceleration along different spatial axes from the vector magnitude signal, a respiration signal determination unit for determining a respiration signal indicative of the respiration of the subject by filtering the non-respiratory motion contribution from at least one of the accelerometer signals.

Preferably, the respiration signal determination unit comprises an adaptive noise filter or an adaptive notch filter.

It shall be understood that the advantages of apparatus according to the invention are similar to the advantages of the method according to the invention, and that additional features of further embodiments of the apparatus according to the invention are similar to the features of the further embodiments of the method according to the invention.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF EMBODIMENTS

To monitor or determine the respiration of a person, in particular under ambulatory conditions, a multi-axial accelerometer, in particular a tri-axial accelerometer, is positioned at the chest or abdomen of a person. A preferred position of a multi-axial accelerometer for respiration monitoring is at the lower ribs, roughly halfway between the central and lateral position. This position provides the most consistent respiration-induced changes in the accelerometer data. Other positions, for example on the abdomen, are also possible in case of limitations due to body physique, for example due to post-surgery wounds.

The multi-axial accelerometer is used as an inclinometer to reflect the movement of the object, in particular, to reflect the movement of the abdomen or the chest caused by respiration. The movement is reflected by an inclination change of a surface of the object, on which the multi-axial accelerometer is positioned. The several different spatial axes of the multi-axial accelerometer, which are preferentially three orthogonal axes, record the accelerometer signals equal to the projection of the gravity vector on each of these axes.

Figure 1A:
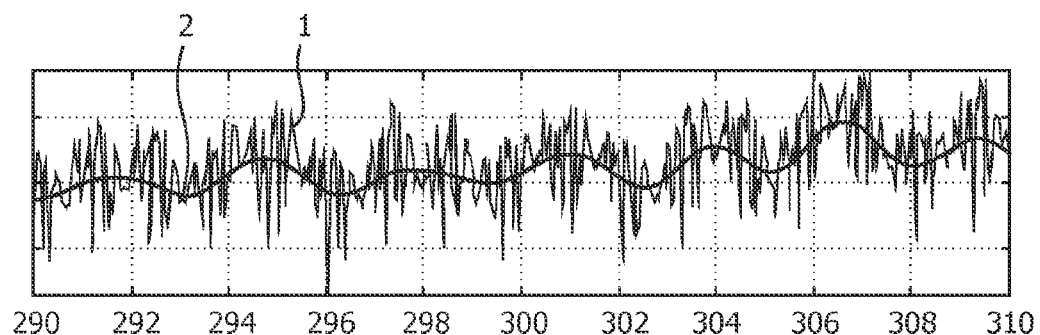
FIG. 1 shows schematically an example of graphs of a single axis accelerometer signal, the extracted vector magnitude signal, a heart beat reference signal and a respiration reference signal.
Figure 1B:
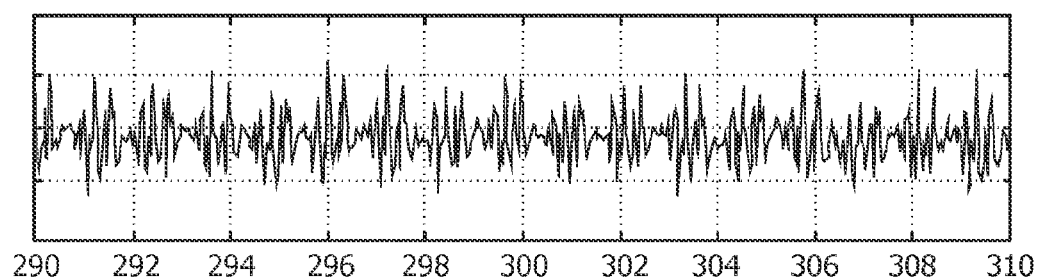
Figure 1C:
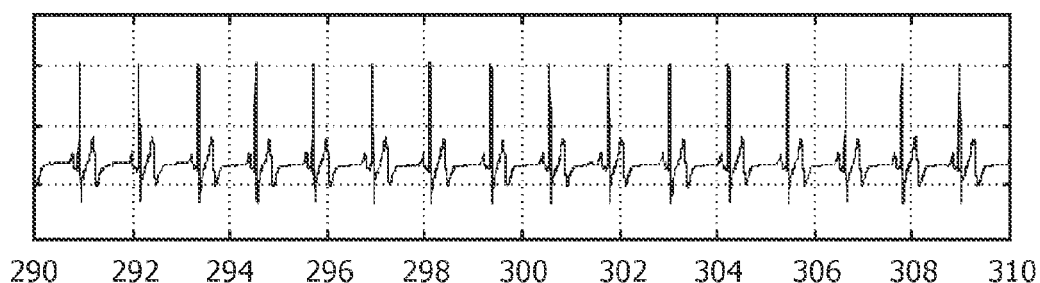
Figure 1D:
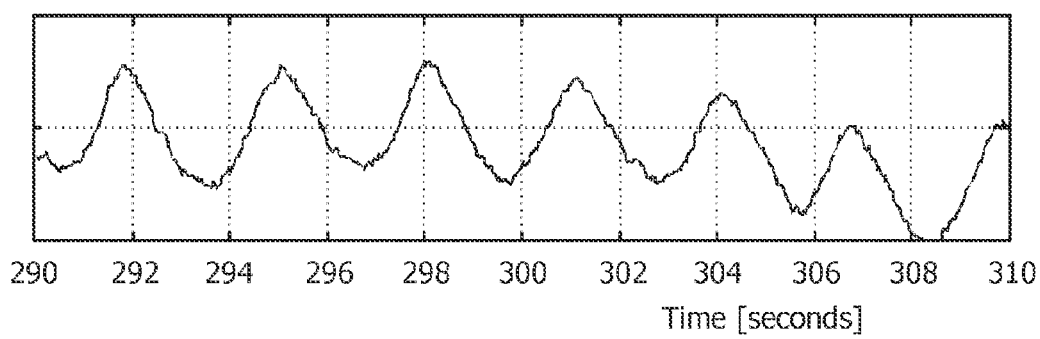

To illustrate the different characteristics of an accelerometer signal due to respiration and heart beat movements, FIG. 1a shows an example of a raw single-axis accelerometer signal 1 as a function of time of one axis of the multi-axial accelerometer positioned on the left side of the thorax of a person. The accelerometer signal 1 is affected both by the respiration movement and by the beating of the heart. A slowly fluctuating signal is recognisable in the accelerometer signal 1 and is indicated in FIG. 1a by curve 2. This slowly fluctuating signal is caused by movement of the thorax due to the respiration, and is related to orientation changes of the multi-axial accelerometer with respect to gravity. Since the respiration movement of the thorax is a slow, smooth movement, the inertial changes of the multi-axial accelerometer caused by the respiratory movement are much smaller than the orientation changes of the multi-axial accelerometer due to respiration movements. In addition to the slowly fluctuating signal due to the respiration, short bursts of a rapidly fluctuations can be observed in the raw accelerometer signal 1. These rapid fluctuations are caused by movement of the thorax due to the beating of the heart and have a much larger inertial component than the fluctuations due to the respiration movements. This larger inertial component in or contribution to the accelerometer signals is visible in FIG. 1b, which shows the vector magnitude signal calculated from the, in this example, accelerometer signals from all three axes of the accelerometer as a function of time, including the single axis accelerometer signal 1 of FIG. 1a. The vector magnitude signal clearly shows only the characteristic rapid fluctuations due to the heart beat movements. The slowly fluctuating movement due respiration, which is mainly due to orientation changes and which has a smaller inertial component than that of the heart beat movements, cannot be discerned or recognised in the vector magnitude signal. As a reference, FIG. 1c shows a corresponding heart beat signal measured with ECG as a function of time and FIG. 1d shows a corresponding respiration signal measured with a respiration belt as a function of time. The heart beat signal and the respiration signal are measured simultaneously with and on the same person as the measurements of the multi-axial accelerometer. The slowly fluctuating signal, which is shown in FIG. 1a by curve 2, and the reference respiration signal, which is shown in FIG. 1d and is measured simultaneously with the respiration belt, clearly have a good correlation. Furthermore, the vector magnitude signal of FIG. 1b shows a good correlation with the heart beat signal of FIG. 1c.

Although most of the power due to the heart beating movements in the accelerometer signal is at frequencies that are outside the normal respiration frequencies, i.e. around 10 Hz, in some cases there is also a non-negligible component at the fundamental heart rate frequency, which is around 1 Hz. Because this fundamental heart rate frequency component is within the frequency range of normal breathing, which is between 0.1 Hz and 2 Hz or between 6 respirations per minute and 120 respirations per minute, it can be erroneously classified as a signal due to respiration whereas in reality it is a signal caused by heart beat movements at the fundamental heart rate frequency. Because both heart rate and respiration rate vary from person to person and also vary as a function of time, this unwanted cardiac interference at the fundamental heart rate frequency, which is within the frequency range of normal breathing, can not be removed from the accelerometer signal by using a filter with a fixed frequency response.

Figure 2:
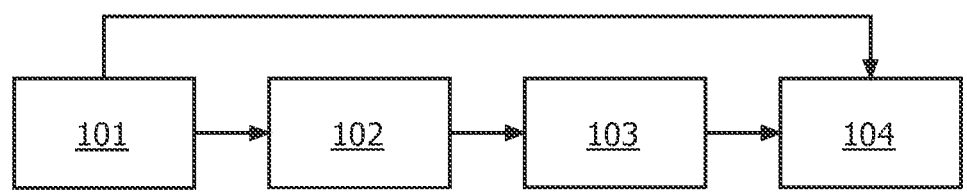
FIG. 2 shows schematically an embodiment of the method according to the invention.

FIG. 2 shows schematically a first embodiment of a method for determining the respiration of a person according to the invention. In step 101 three accelerometer signals are measured with one tri-axial accelerometer positioned at a suitable position on the body of a person, in this example on the thorax. The three measured accelerometer signals comprise information on the movement of the thorax due to respiration and due to non-respiratory movement or motion of the thorax, such as the heart beat, along three different axes, for example three orthogonal axes. The raw accelerometer signals measured in step 101 are used in step 102 in which the vector magnitude signal of the three raw accelerometer signals is calculated. The vector magnitude can for example be calculated by taking the vector sum of the three accelerometer signals representing the three different axes:

$$m(t)=\sqrt{[x(t)^2+y(t)^2+z(t)^2]}$$

where m(t) represents the vector magnitude of the accelerometer at time instant t, and x(t), y(t) and z(t) represent the acceleration as measured in respectively the X-, Y- and Z-axis of the accelerometer at time instant t. In step 103 a noise reference signal is extracted from the vector magnitude signal which was determined in step 102 by a digital filtering technique. For example, the noise reference signal is determined by calculating the envelope of the vector magnitude signal, by first filtering the vector magnitude signal with a band-pass filter, for example between 5 Hz and 15 Hz, to remove base line wander and high-frequency noise, by subsequently rectifying the vector magnitude signal by calculating the absolute values or by squaring, and finally by filtering the absolute or squared values with a low-pass filter, for example with a limit of 2 Hz, to remove high-frequency noise outside the range of physiologically realistic respiration rates. The noise reference signal represents the motion or movements of the thorax that are not due to respiration, because the slowly fluctuating respiration signal with the relatively small inertial component has a negligible contribution in the vector magnitude signal, whereas the motion of the thorax due to the heart beat will have a relatively large inertial component and thus a relatively large contribution to the vector magnitude signal. Finally in step 104 the noise reference signal and at least one of the raw accelerometer signals is used in an adaptive noise canceller to filter the unwanted noise, mainly corresponding to the heart beat movements, from at least one of the raw accelerometer signals resulting in a signal that represents the respiration of the person in a reliable and more accurate way. The adaptive filtering can also be applied for each of the three accelerometers signals separately, after which an appropriate combination of the three filtered accelerometer signals results in the respiration signal. In this way, the cardiac interference is removed from the accelerometer signals without an external reference for determining the cardiac interference. Other approaches for calculating the envelope relying on for example the Hilbert transform or the short-time Fourier transform may also be used.

Figure 3A:
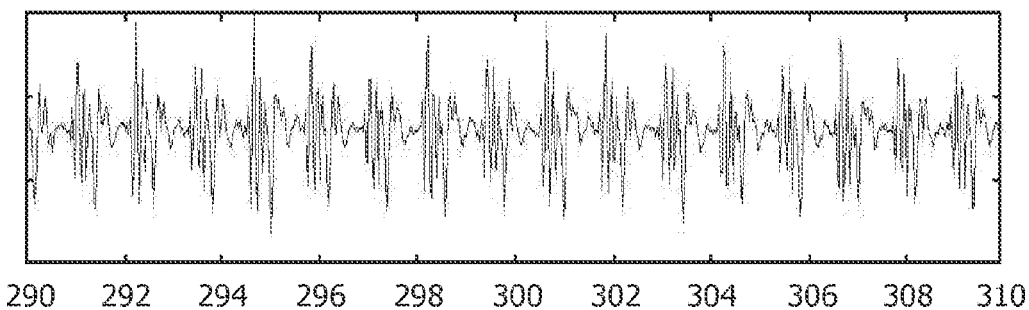
FIG. 3 shows schematically an example of graphs of a vector magnitude signal, a filtered vector magnitude signal, the absolute values of the filtered vector magnitude signal and an extracted noise reference signal according to an embodiment of the invention.
Figure 3B:
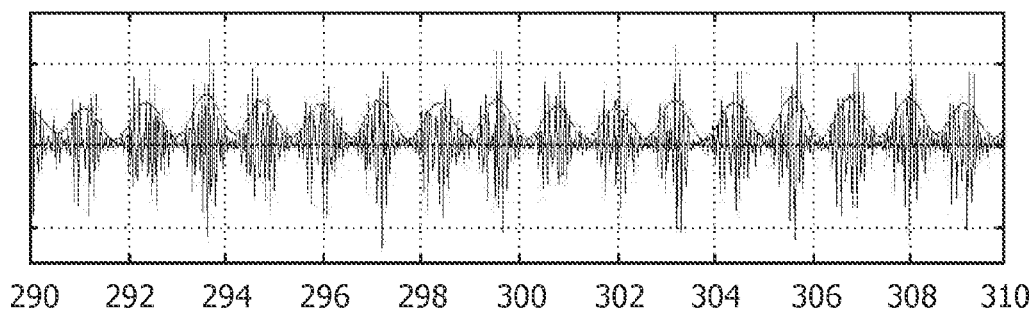
Figure 3C:
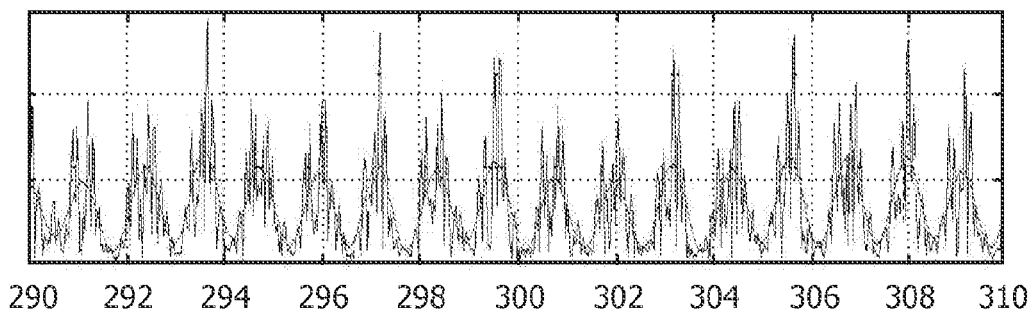
Figure 3D:
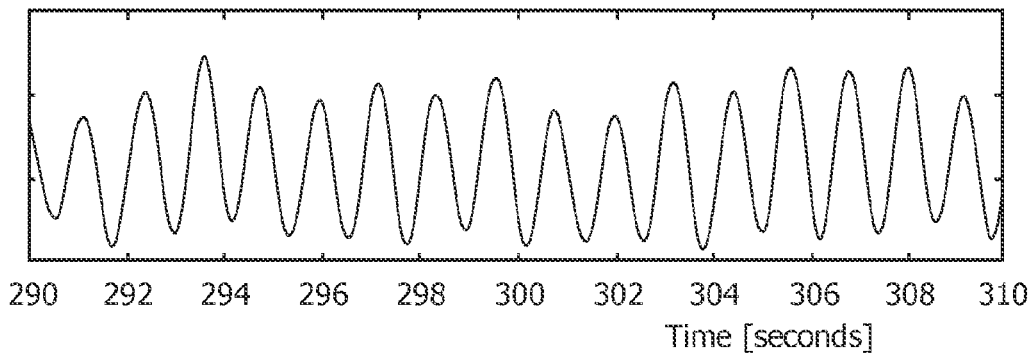

The basic idea of the next embodiment is to transform the vector magnitude signal into a signal, i.e. the noise reference signal, which corresponds to the cardiac interference signal at the fundamental heart frequency, and to use this signal as the noise reference in an adaptive noise cancelling scheme. FIGS. 3a-d show an example of how the accelerometer signals and the vector magnitude signal are used to extract the noise reference signal by applying a digital filtering technique, in this example by taking the envelope of the vector magnitude signal. FIG. 3a shows a graph of a vector magnitude signal as a function of time calculated from the accelerometer signals from all three axes of the tri-axial accelerometer. FIG. 3b shows a graph of the accelerometer vector magnitude signal of FIG. 3a that is filtered with a band-pass filter with a pass band between 5 Hz and 15 Hz to remove baseline wander and high-frequency noise. FIG. 3c displays a graph of the absolute value of the filtered accelerometer vector magnitude signal of FIG. 3b. Alternatives, like for example squaring of the data, can also be applied to obtain this result. FIG. 3d displays a graph showing the low-pass filtered version of the absolute value of the graph of FIG. 3c, wherein the low-pass filter has a cut-off frequency of, for example, 2 Hz. The graph of FIG. 3d represents a noise reference signal extracted from the vector magnitude signal according to the method of FIG. 2. From FIG. 3d it is clear that it is also possible to derive the heart rate or frequency in this way from the vector magnitude envelope, and use this to selectively remove the cardiac interference at the fundamental heart frequency with a suitable filter. Optionally also the first and other harmonics can be filtered. For example, an adaptive notch filter or a comb filter can be applied. This adaptive filtering method significantly reduces the cardiac interference in accelerometer signals.

Figure 4A:
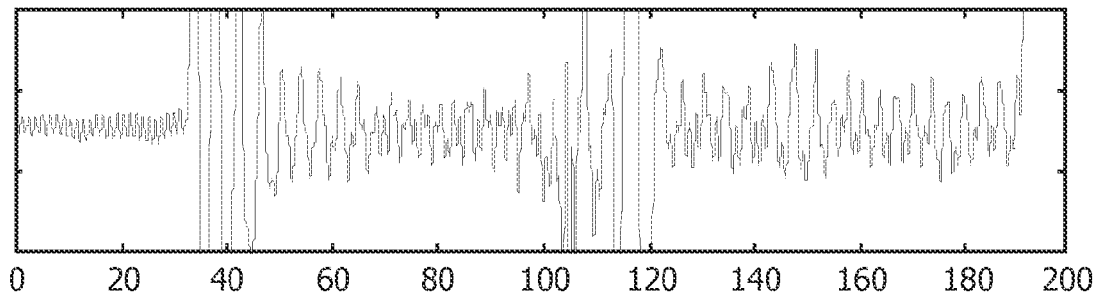
FIG. 4 shows schematically an example of graphs of a single axis accelerometer signal, the filtered single axis accelerometer signal and a respiration reference signal according to an embodiment of the invention.
Figure 4B:
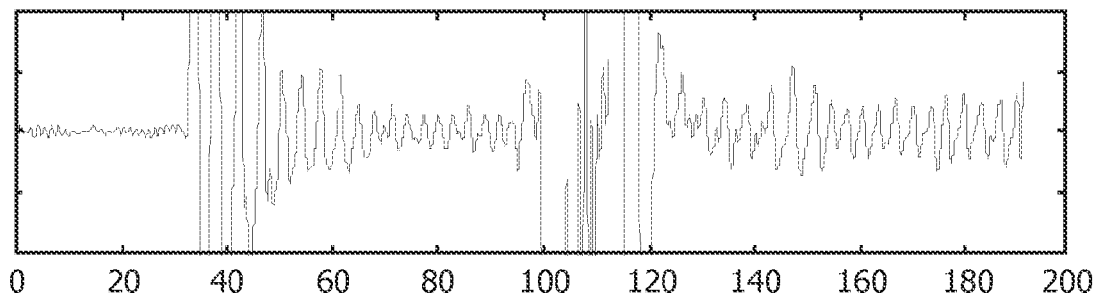
Figure 4C:
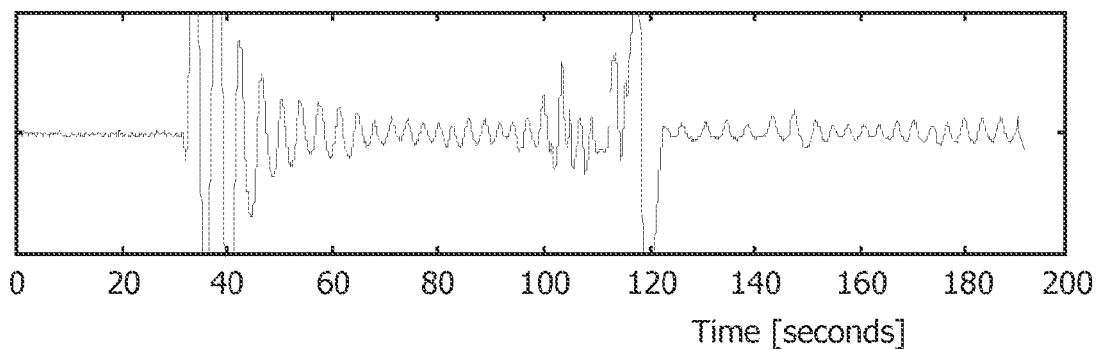

FIG. 4 illustrates the results of another example of the adaptive filtering method. FIG. 4a displays a single axis accelerometer signal as a function of time that has been filtered with a band-pass filter covering the normal respiratory frequency range, for example between 0.1 Hz and 2 Hz. FIG. 4b illustrates the single axis accelerometer signal after it has been processed with the adaptive noise filter. FIG. 4c shows a corresponding reference respiration signal measured with a respiration belt as a function of time and which is measured simultaneously with and on the same person as the measurements of the multi-axial accelerometer. The first 30 seconds of the signals cover a period of apnea, followed by a period of recovery and normal breathing. By comparing FIG. 4a with FIG. 4b in the first 30 seconds it is observed that the amplitude of the cardiac interference during the apnea period is reduced by a factor of 2 using the adaptive noise filtering method. Furthermore, during normal breathing the accelerometer signal waveform contains a smaller amount of peaks due to the cardiac interference.

Besides respiration and heart beat, the accelerometer signal is also affected by other types of body movement such as for example walking or running. The accelerometer signal changes associated with respiration are mainly due to orientation changes in relation to the gravity direction. The other types of body movement, such as walking or running, induce changes in the accelerometer signal that are not only due to orientation changes but also have a relative large inertial component compared to the inertial component due to respiration movements. These inertial components can be identified based on the vector magnitude of the accelerometer signal, and then again be used to suppress the other motions in the accelerometer signals of each axis in order to obtain a clean and reliable respiration signal.

Figure 5:
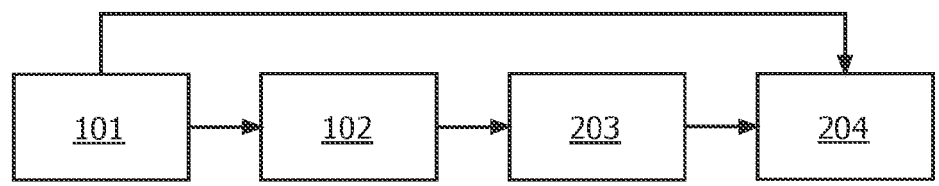
FIG. 5 shows schematically an embodiment of the method according to the invention.

FIG. 5 illustrates schematically a second embodiment of the method of determining the respiration of a person according to the invention. In step 101 three accelerometer signals are measured with one tri-axial accelerometer positioned at a suitable position on the body of a person, in this example the thorax. The three measured accelerometer signals comprise information of the movement of the thorax due to respiration and, in this example, due to movement of the person along three different axes, for example three orthogonal axes. The raw accelerometer signals measured in step 101 are used in step 102 in which the vector magnitude signal is calculated from the three raw accelerometer signals. The vector magnitude can for example be calculated by taking the vector sum of the three accelerometer signals representing the three different axes. In step 203 a characteristic frequency is extracted from the vector magnitude signal that was determined in step 102. Optionally, in step 203 first the vector magnitude signal is filtered with a band-pass filter, for example between 0.1 Hz and 1 Hz, to remove all noise outside a respiration range that is physiologically realistic for a specific person. In step 203 the characteristic frequency is extracted, for example by a power spectrum of the vector magnitude signal or by a coherence spectrum of the vector magnitude signal and of one of the accelerometer signals. The characteristic frequency is a frequency that is characteristic, in this example, for the movement of the person, for example the step frequency during walking or running. The movement of the person, i.e. walking or running, will have a relatively large contribution to the vector magnitude signal because the inertial acceleration due to the walking is larger than the inertial acceleration due to the respiration movements. Hence, the frequency analysis of the vector magnitude signal, for example via the power spectrum or the coherence spectrum, will reveal a dominant frequency that represents the contribution with the largest inertial acceleration, which is in this case due to the walking or running of the person. Finally in step 204 the characteristic frequency and the raw accelerometer signals are used in a suitable filter to filter the unwanted noise, in this case mainly corresponding to walking, from the raw accelerometer signals resulting in a signal that reliably and accurately represents the respiration of the person. For example, in step 204 an adaptive notch filter or a comb filter is applied in which the characteristic frequency and, optionally, its higher harmonics are filtered. The filtering can be applied for each of the three accelerometers signals separately, after which an appropriate combination of the three filtered accelerometer signals results in the respiration signal. In this way, the interference or noise due to body movements of the person is removed from the accelerometer signals without requiring an external reference for measuring the body movements, such as for example an extra accelerometer.

Figure 6A:
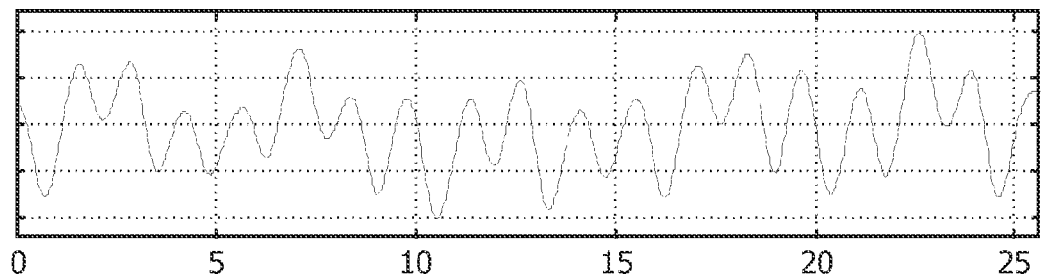
FIG. 6 shows schematically an example of graphs of a single axis accelerometer signal, the filtered single axis accelerometer signal and a respiration reference signal according to an embodiment of the invention.
Figure 6B:
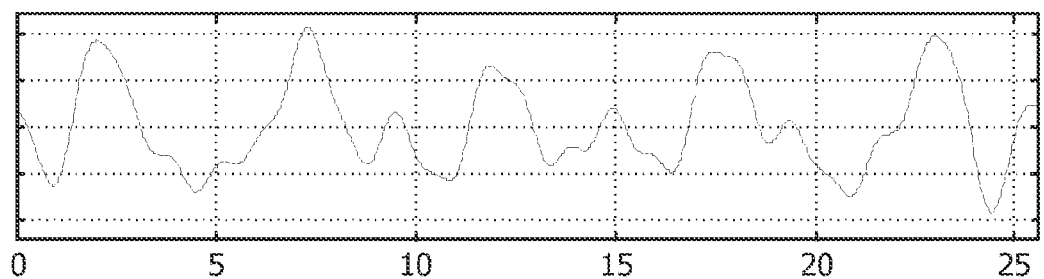
Figure 6C:
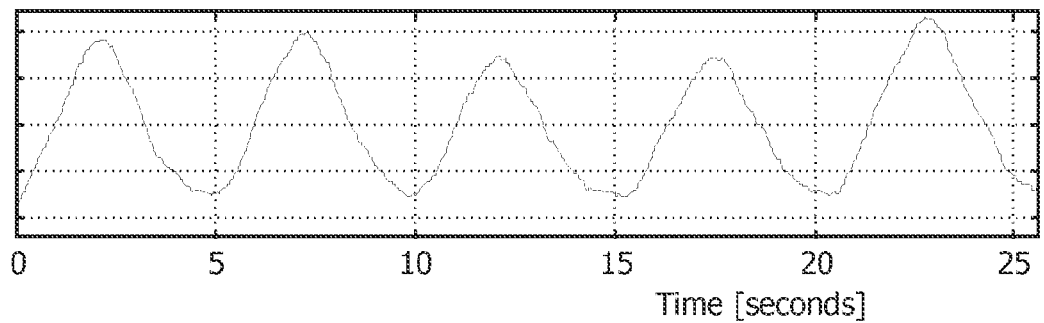

FIG. 6 illustrates an example of the frequency filtering method illustrated in FIG. 5. FIG. 6a displays a single axis accelerometer signal as a function of time of a walking person wherein the signal has been filtered with a band-pass filter covering a normal respiratory frequency range for a specific person, for example between 0.1 Hz and 1 Hz. FIG. 6b illustrates the single axis accelerometer signal after it has been processed with the adaptive notch filter. FIG. 6c shows a corresponding reference respiration signal measured with a respiration belt as a function of time and which is measured simultaneously with and on the same person as the measurements of the multi-axial accelerometer. In the filtered signal shown in FIG. 6b the fluctuations due to the respiration can clearly be observed and the respiration rate can easily be determined by, for example, a peak detection algorithm. As can be seen from FIG. 6a the dominant frequency in the accelerometer signal has a period of about 1.4 seconds which corresponds to approximately 0.72 Hz. These fluctuations, however, are not due to the respiration of the person but are due to the walking of the person with a stride frequency of 0.72 Hz, wherein one stride consists of 2 steps, one with each foot, whereas the true respiration rate is about 0.18 Hz, corresponding to about 11 respirations per minute as can be observed from the respiration band signal in FIG. 6c. The acceleration associated with each foot touching the ground has a large inertial component. The component in or contribution to the acceleration signals as a consequence of the stride of the person is due to the orientation changes of the upper body associated with each stride, which corresponds to two steps. Because the stride acceleration changes occur relatively smoothly, the inertial component associated with the stride is relatively small. Because every step is associated with a larger inertial acceleration than the respiration, the step and the stride frequency can be derived from the analysis of the vector magnitude signal. Once the fundamental step and stride frequency is identified from the accelerometer vector magnitude, an adaptive notch or a comb filter is used to remove this frequency and eventually it's first harmonics from one or more of the raw accelerometer signals. In this way the respiration rate can be extracted in a reliable way while at the same time the step frequency is determined of a moving, for example walking or running, person.

Figure 7:
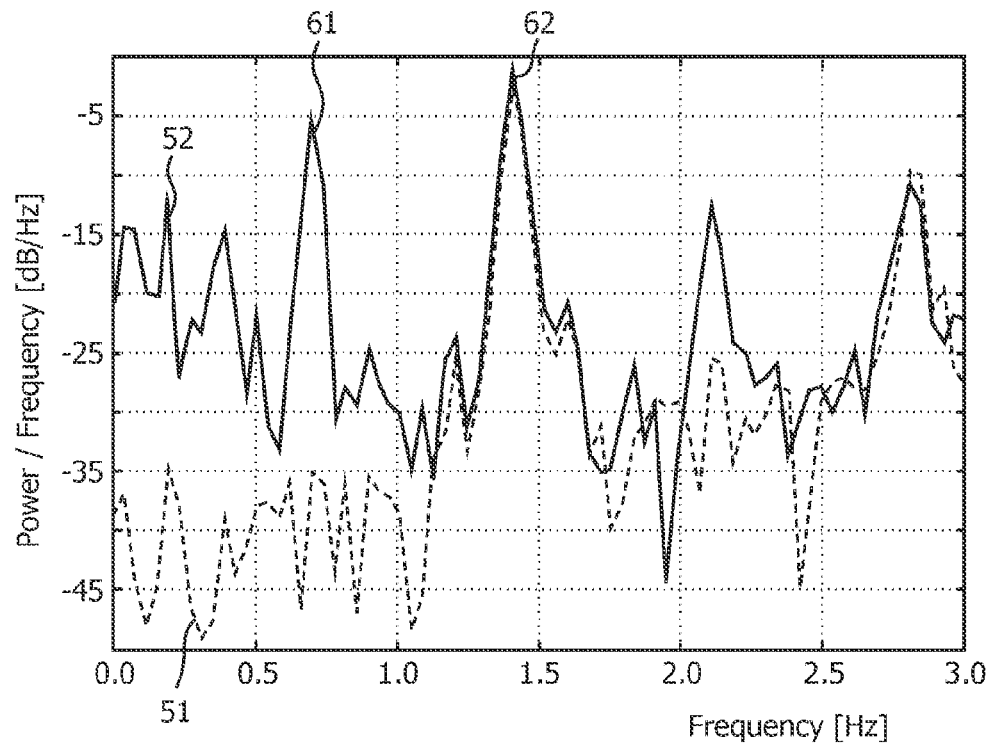
FIG. 7 shows schematically and exemplarily an example of a power spectrum according to an embodiment of the invention.

FIG. 7 illustrates an example of power spectra graphs calculated from the accelerometer signal data of a walking person as shown in FIG. 6. A power spectrum represents the magnitude, for example squared, of a Fourier transformed signal. In FIG. 7 the vertical axis represents the power divided by the frequency in [dB/Hz] and the horizontal axis represents the frequency in [Hz]. The first power spectrum 51 is calculated from the vector magnitude signal and the second power spectrum 52 is calculated from the raw data of, in this case, the Z-axis accelerometer signal. From FIG. 7 it is clear that the dominant frequency in the accelerometer vector magnitude is the step frequency, corresponding to two times the stride frequency, because every step is associated with a relatively large inertial acceleration. The highest peak of the power spectrum 51 of the vector magnitude signal is identified as the step frequency, which is in this case peak 62. The fact that the height of the peak 62 is comparable for the first power spectrum 51 and the second power spectrum 52 shows that the peak 62 represents for the main part inertial acceleration. First peak 61, which is only visible in the second power spectrum 52 of the single axis accelerometer signal, and which peak 61 is the second largest, represents the stride frequency which is half of the step frequency. The component in or contribution to the acceleration caused by the stride is due to the orientation changes of the upper body associated with each stride. Because these acceleration changes due to the stride occur relatively smoothly, the inertial component, or contribution, associated with the stride is relatively small, especially compared to the inertial component, or contribution, caused by each step of the subject. Therefore, the peak 61 associated with the stride frequency is only visible in the power spectrum 52 of the individual axes accelerometer signal and not in the power spectrum 51 of the vector magnitude signal. Because the stride frequency is at exactly half of the step frequency, it is clear that this frequency component is associated with the relatively large inertial component due to, in this case, walking rather than due to the respiration. Similarly the higher harmonics peaks, for example at 2.1 Hz and 2.8 Hz, are associated with the relatively large acceleration due to, in this example, walking. The peak at 2.1 Hz mainly represents orientation changes whereas the peak at 2.8 Hz is mainly due to inertial acceleration. The difference in the magnitude or power of the peak 62 at the step frequency and the magnitude of the respiration peaks of the first power spectrum 51 is about 35 dB, which corresponds to an approximately fifty times larger inertial contribution of the movements due to the walking than the inertial contribution due to respiration. Alternatively or simultaneously the power spectrum is used to extract the heart beat frequency of the subject while the subject is walking or running. In this way the respiration of a moving person can be extracted in a reliable way while simultaneously also the step frequency and/or the heart beat frequency of the moving person are determined.

Figure 8:
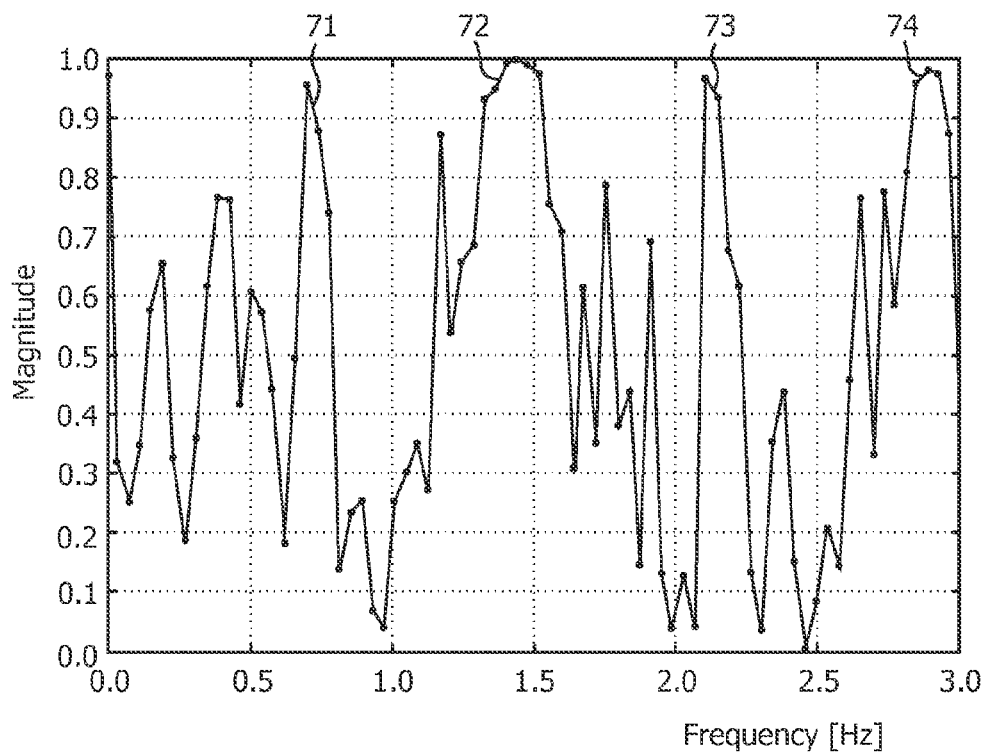
FIG. 8 shows schematically and exemplarily an example of a coherence spectrum according to an embodiment of the invention.

FIG. 8 illustrates an example of a coherence spectrum calculated from the data and signals of a walking person as shown in FIG. 6. In FIG. 8 the vertical axis represents the coherence between two signals and the horizontal axis represents the frequency in [Hz]. The coherence is a normalized cross-spectral density of two signals, which results in values between zero and one that indicates how well two signals correspond, or, in other words, are a measure of the similarity of two signals, at a specific frequency, wherein the highest coherence value corresponds to the largest similarity or matching between the two signals. The coherence is for example calculated by using Welch's averaged, modified periodogram method. FIG. 8 displays a graph which represents the coherence spectrum between the accelerometer vector magnitude and the accelerometer signal of an individual axis. It can be observed from peaks 71, 72, 73 and 74 that the coherence has a value above 0.9 at both the step frequency and the stride frequency, whereas at the respiration frequency the coherence has a value below 0.8. If the similarity between the vector magnitude signal and the single axis accelerometer signal is high at a specific frequency, thus showing a high coherence value, then in this case at that specific frequency the inertial contribution to the single axis accelerometer signal is relatively large. Because the vector magnitude signal is representative for the inertial contributions with the relatively largest values, a high coherence value corresponds to and represents the largest inertial contribution, which is in this example the inertial contribution due to walking. A similar approach can be used to filter alternatively or simultaneously the inertial contributions due to heart beat movements by extracting the heart beat frequency from the vector magnitude signal using for example the power spectrum and/or coherence spectrum methods.

Figure 9:
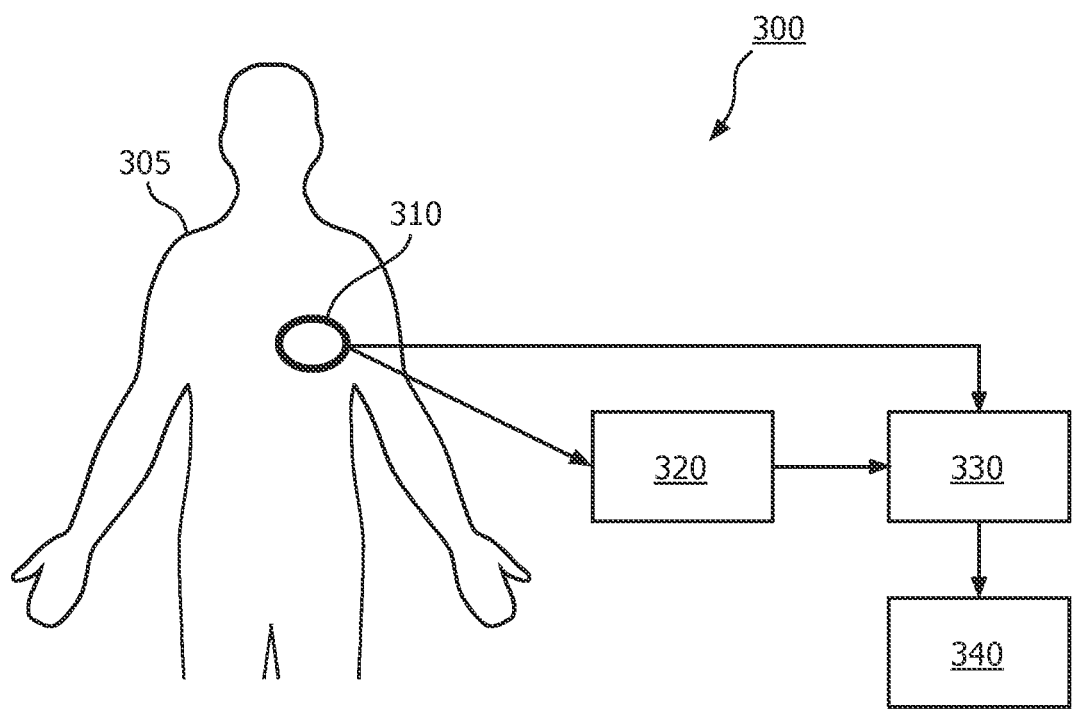
FIG. 9 shows schematically an embodiment of the apparatus according to the invention.

An embodiment of a respiration determination apparatus for determining a respiration of a subject 305 according to the invention is illustrated in FIG. 9. The respiration determination apparatus 300 comprises a single multi-axial accelerometer 310 that is positioned at a body of the subject 305, for example on the thorax of a person. The multi-axial accelerometer 310 generates accelerometer signals that are indicative of the acceleration along different spatial axes of the, in this example, thorax of the person. A signal processing unit 320 calculates a vector magnitude signal of the acceleration along the different spatial axes from the accelerometer signals. Furthermore, the signal processing unit 320 identifies a non-respiratory motion contribution to the acceleration along different spatial axes from the vector magnitude signal. The non-respiratory motion contribution is, for example, the movement of the thorax due to heartbeat or due to movement of the person in the form of walking or running. A respiration signal determination unit 330 determines a respiration signal that is indicative of the respiration of the subject by filtering the non-respiratory motion contribution from the accelerometer signals. For example, the filtering is done with an adaptive noise or notch filter or a comb filter. Finally the respiration signal can be displayed on a display 340.

Although in the above described embodiments the multi-axial accelerometer has preferentially three orthogonal axes, the multi-axial accelerometer can also have two orthogonal axes or more than three axes. Furthermore, the spatial axis can also include another angle, i.e. in another embodiment the axes can be non-orthogonal.

Although in the above described embodiments, one multi-axial accelerometer is used, also two or more multi-axial accelerometers according to the invention can be used to be able determine the respiration signal with an even greater accuracy and each applying the method according to the invention.

The frequency ranges and values that are used in the embodiments according to the invention may be parameters that are set by a user, for example depending on the type of subject, e.g. age, for which the respiration is determined.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A method for monitoring a respiration of a subject comprising the steps of:
   generating, with a single multi-axial accelerometer positioned on a body of the subject, accelerometer signals indicative of the acceleration of the subject along different spatial axes,
   calculating, with at least one processor, a vector magnitude signal of the acceleration of the subject as a magnitude of the vector sum of the accelerometer signals along the different spatial axes,
   identifying, with the at least one processor, from the vector magnitude signal of the acceleration a non-respiratory motion contribution to the acceleration along the different spatial axes which non-respiratory motion contribution is not caused by the respiration, the non-respiratory motion being indicative of at least a motion of a thorax due to cardiac activity of the subject,
   filtering, with the at least one processor, the non-respiratory motion contribution from at least one of the accelerometer signals;
   determining, with the at least one processor, a respiration signal indicative of the respiration of the subject with the at least one filtered accelerometer signal; and
   displaying the determined respiration signal on a display.

2. The method as defined in claim 1, wherein the step of determining the respiration signal includes the steps of:
   filtering the non-respiratory motion contribution from each of the accelerometer signals separately,
   determining the respiration signal from a combination of the filtered accelerometer signals.

3. The method as defined in claim 1, wherein the step of identifying the non-respiratory motion contribution comprises the steps of:
   calculating a power spectrum of the vector magnitude signal,
   extracting a characteristic frequency of the non-respiratory motion from the power spectrum,
   and wherein the step of determining the respiration signal comprises a step of filtering the characteristic frequency from the accelerometer signals with an adaptive notch filter.

4. The method as defined in claim 1, wherein the step of identifying the non-respiratory motion contribution comprises the steps of:
   calculating a coherence spectrum of the vector magnitude signal and one of the accelerometer signals,
   extracting a characteristic frequency of the non-respiratory motion contribution from the coherence spectrum,
   and wherein the step of determining the respiration signal comprises a step of filtering the characteristic frequency from the accelerometer signals with an adaptive notch filter.

5. The method as defined in claim 1, further comprising a step of extracting a respiration rate of the subject from the respiration signal.

6. The method as defined in claim 1, further comprising a step of filtering a frequency range from the vector magnitude signal which filtered vector magnitude signal is used in the step of identifying the non-respiratory motion contribution.

7. The method as defined in claim 1, wherein the step of identifying the non-respiratory motion contribution comprises a step of extracting a characteristic frequency of the non-respiratory motion contribution from the vector magnitude signal.

8. The method as defined in claim 7, wherein the characteristic frequency of the non-respiratory motion contribution comprises a heart beat frequency of the subject.

9. The method as defined in claim 7, wherein the characteristic frequency of the non-respiratory motion contribution comprises a step frequency of a moving subject.

10. The method as defined in claim 1, wherein the step of identifying the non-respiratory motion contribution comprises a step of extracting a noise reference signal representative for the unwanted noise contribution from the vector magnitude signal.

11. The method as defined in claim 10, wherein the noise reference signal is extracted from the vector magnitude signal with a digital filtering technique.

12. The method as defined in claim 10, wherein the noise reference signal comprises a cardiac interference signal.

13. The method as defined in claim 10, wherein the step of determining the respiration signal comprises a step of filtering the accelerometer signals with an adaptive noise filter with the noise reference signal.

14. The method as defined in claim 10, wherein the step of identifying the non-respiratory motion contribution further comprises a step of extracting a characteristic frequency of the non-respiratory motion contribution from the noise reference signal and wherein the step of determining the respiration signal comprises a step of filtering the characteristic frequency from the accelerometer signals with an adaptive notch filter.

15. A respiration monitoring apparatus for monitoring a respiration of a subject, wherein the respiration monitoring apparatus comprises:
   a single multi-axial accelerometer configured to be positioned on a body of the subject, wherein the multi-axial accelerometer is adapted to generate accelerometer signals $x(t)$, $y(t)$, and $z(t)$ indicative of the acceleration of the subject along orthogonal x, y, and z spatial axes respectively,
   a signal processing unit programmed to calculate a vector magnitude signal $m(t)$ of the acceleration of the subject as $m(t)=\sqrt{x(t)^2+y(t)^2+z(t)^2}$ and for identifying a non-respiratory motion contribution to the acceleration along different spatial axes from the vector magnitude signal $m(t)$, the non-respiratory motion being indicative of at least a motion of a thorax due to a cardiac activity of the subject,
   a respiration signal determination unit programmed to:
   filter the non-respiratory motion contribution from at least one of the accelerometer signals; and
   determine a respiration signal indicative of the respiration of the subject with the at least one filtered accelerometer signal; and
   a display on which the determined respiration signal is displayed.

16. The respiration monitoring apparatus of claim 15, wherein the respiration signal determination unit is further programmed to:
   filter the non-respiratory motion contribution from each of the accelerometer signals separately, determine the respiration signal from a combination of the filtered accelerometer signals.

17. The respiration monitoring apparatus of claim 15, wherein the signal processing unit is further programmed to
extract a characteristic frequency of the non-respiratory motion contribution from the vector magnitude signal;
wherein the characteristic frequency of the non-respiratory motion contribution comprises a heart beat frequency of the subject.

18. The respiration monitoring apparatus of claim 15, wherein the signal processing unit is further programmed to:
extract a noise reference signal representative for the unwanted noise contribution from the vector magnitude signal
wherein the noise reference signal comprises a cardiac interference signal.

19. A respiration monitoring apparatus for determining a respiration of a subject, wherein the respiration monitoring apparatus comprises:
a single multi-axial accelerometer configured to be positioned on a body of the subject, wherein the multi-axial accelerometer is adapted to generate accelerometer signals indicative of the acceleration of the subject along different spatial axes,
a signal processor programmed to calculate a vector magnitude signal of the acceleration of the subject as a magnitude of the vector sum of the accelerometer signals along the different spatial axes and for identifying a non-respiratory motion contribution to the acceleration along different spatial axes from the vector magnitude signal,
a respiration signal determination processor programmed to filter the non-respiratory motion contribution from at least one of the accelerometer signals, and determine a respiration signal indicative of the respiration of the subject with the at least one filtered accelerometer signal; and
a display on which the determined respiration signal is displayed;
wherein the non-respiratory motion contribution comprises a cardiac interference signal.

20. The respiration monitoring apparatus of claim 19, wherein the respiration signal determination processor is further programmed to:
filter the non-respiratory motion contribution from each of the accelerometer signals separately,
determine the respiration signal from a combination of the filtered accelerometer signals.

* * * * *